United States Patent [19]

Drejer et al.

[11] Patent Number: 5,019,582
[45] Date of Patent: May 28, 1991

[54] PIPERIDINE COMPOUNDS AND THEIR PREPARATION AND USE

[75] Inventors: Jorgen Drejer, Bronshoj; Palle Jakobsen, Vaerlose, both of Denmark

[73] Assignee: Novo Nordisk A/S, Bagsvaerd, Denmark

[21] Appl. No.: 407,237

[22] Filed: Sep. 14, 1989

Related U.S. Application Data

[62] Division of Ser. No. 106,154, Oct. 8, 1987, Pat. No. 4,877,799.

[30] Foreign Application Priority Data

Nov. 3, 1986 [DK] Denmark .............................. 5232/86
Jun. 25, 1987 [DK] Denmark .............................. 3234/87

[51] Int. Cl.$^5$ ................. C07D 405/12; C07D 211/22; A61K 31/445; A61K 31/395
[52] U.S. Cl. ....................... 514/321; 514 317;319/546; 546/197; 546/198; 546/206; 546/236
[58] Field of Search ............... 546/197, 198, 206, 236; 514/317, 319, 321

[56] References Cited

U.S. PATENT DOCUMENTS 3,912,743 10/1975 Christensen .......................... 546/197
4,007,196  2/1977 Christensen et al. ................ 546/197

FOREIGN PATENT DOCUMENTS 152273  7/1984 European Pat. Off. ............ 546/236
223403 10/1985 European Pat. Off. ............ 546/197

Primary Examiner—Mary C. Lee
Assistant Examiner—Lenora Miltenberger
Attorney, Agent, or Firm—Gordon W. Hueschen

[57] ABSTRACT

Novel piperidine compounds having the formula

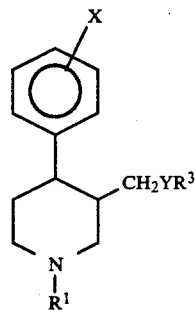

wherein

R$^3$ is 3,4-methylenedioxyphenyl, aryl or heteroaryl which are optionally substituted with one or more C$_{1-6}$-alkyl, C$_{1-6}$-alkoxy, C$_{3-8}$-cycloalkyl, C$_{3-5}$-alkylene or aralkoxy, R$^1$ is straight or branched C$_{1-8}$-alkyl, C$_{4-8}$-alkoxy-C$_{4-8}$-alkyl, C$_{4-7}$-cycloalkyl, aryloxy-C$_{3-8}$-alkyl, C$_{4-8}$-alkenyl, or C$_{4-8}$-cycloalkylalkyl, or R$^1$ may also be hydrogen or C$_{1-3}$-alkyl, when R$^3$ is aryl, which is substituted with two or more of C$_{1-6}$-alkyl, C$_{1-6}$-alkoxy, C$_{3-8}$-cycloalkyl, aralkoxy, or with C$_{3-5}$-alkylene.

X is hydrogen or halogen, and wherein

Y is O or S or a salt thereof with a pharmaceutically-acceptable acid, pharmaceutical compositions thereof, method-of-treating therewith.

The novel compounds are useful in the treatment of anoxia, migraine, ischemia and epilepsy.

9 Claims, No Drawings

PIPERIDINE COMPOUNDS AND THEIR PREPARATION AND USE

This is a division of application Ser. No. 106,154, filed Oct. 8, 1987, now U.S. Pat. No. 4,877,799.

The present invention relates to therapeutically active piperidine compounds, a method of preparing the same, pharmaceutical compositions comprising the compounds and to a method of treating therewith The novel compounds are useful in the treatment of anoxia, ischemia, migraine and epilepsy.

It is well known that accumulation of calcium in the brain cells (calcium overload) is seen after periods of uncontrolled hyperactivity in the brain, such as after convulsions, migraine, anoxia and ischemia. As the concentration of calcium in the cells is of vital importance for the regulation of cell function, an uncontrolled high concentration of the cell calcium will lead to, or indirectly cause the symptoms and possibly also the degenerative changes combined with the above diseases.

Therefore calcium overload blockers selective for brain cells will be useful i n the treatment of anoxia, ischemia, migraine and epilepsy.

Well known calcium antagonists such as nifedipine, verapamil and diltiazem have activity against pheripheral calcium uptake, e.g. in blood vessels and the heart, however have shown only very low activity against calcium overload in brain cells.

Accordingly it is an object of the invention to provide novel compounds having activity against calcium overload in brain cells.

The novel compounds of the invention are piperidine compounds having the general formula I

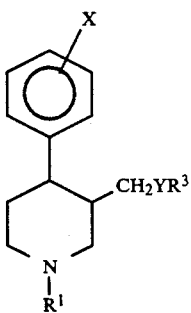

wherein
$R^3$ is 3 4-methylenedioxyphenyl, aryl or heteroaryl which are optionally substituted with one or more $C_{1-6}$-alkyl, $C_{1-6}$-alkoxy, $C_{3-8}$-cycloalkyl, $C_{3-5}$-alkylene or aralkoxy,
$R^1$ is straight or branched $C_{4-8}$-alkoxy-$C_{1-8}$-alkoxy-$C_{4-8}$-alkyl, $C_{4-7}$-cycloalkyl, aryloxy-$C_{3-8}$-alkyl $C_{4-8}$-alkenyl, or $C_{4-8}$-cycloalkylalkyl, or $R^1$ may also be hydrogen or $C_{1-3}$-alkyl, when $R^3$ is aryl, which is substituted with two or more of $C_{1-6}$- alkyl $C_{1-6}$-alkoxy, $C_{3-8}$-cycloalkyl, aralkoxy, or with $C_{3-5}$- alkylene.
X is hydrogen or halogen, and wherein
Y is O or S
or a salt thereof with a pharmaceutically acceptable acid.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts.

The invention also relates to a method of preparing the above mentioned compounds. This methods comprises
a) reacting a compound having the general formula II

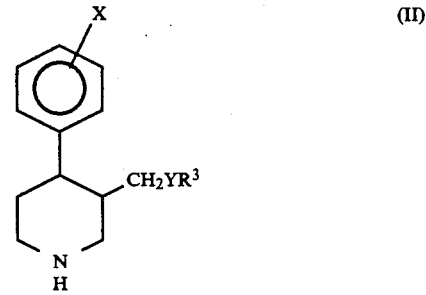

wherein $R^3$, X and Y have the meanings defined above, with a compound having the the general formula $R^1$-Z , wherein Z is a leaving group such as halogen and $R^1$ has the meaning defined above,
b) reacting a compound having the general formula III

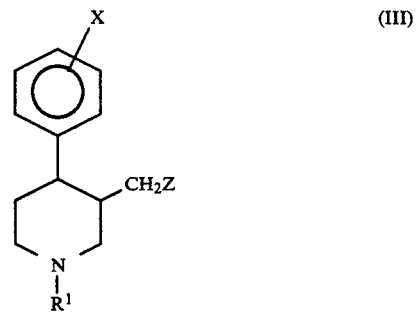

wherein $R^1$ and X have the meanings defined above, and Z is a leaving group, with a compound having the the general formula $R^3$-YH, wherein Y is O or S and $R^3$ has the meaning defined above.

The pharmacological properties of the compounds of the invention can be illustrated by determining their capability to inhibit calcium uptake into brain synaptosomes.

PRINCIPLE

Depolarization of neuronal membranes leads to an opening of socalled 'voltage operated calcium channels' (VOC) in the membranes which allows a massive influx of calcium from the extracellular space. A crude synaptosomal preparation (socalled $P_2$ fraction) contains small vesicles surrounded by neuronal membrane and it is possible in such a preparation to study a depolarization-induced opening of VOC. In the present model $^{45}Ca$ influx is induced in the synaptosomes by depolarization with elevated potassium concentrations, and the effect of test substances on this stimulated uptake is studied (Nachshen, D.A. and Blaustein M P. Mol. Pharmcol. 16, 579 (1979)).

ASSAY

A male Wistar rat is decapitated and the cerebral cortex removed and homogenized in 20 ml. of ice-cold 0.32 M sucrose using a glass homogenizer with a teflon pestle. All subsequent steps for isolation of synaptosomes are done at 0°–4° C. The homogenate is centrifuged at 1000×g for 10 min and the resulting supernatant is re-centrifuged at 18000×g for 20 min. This pellet (P$_2$) is resuspended in 0.32 M sucrose (10 ml per g of original tissue) with a teflon pestle.

Aliquots (0.050 ml) of this crude synaptosomal suspension are added to glass tubes containing 0.625 ml of NaCl buffer (136 mM NaCl, 4 mM KCl, 0.35 mM CaCl$_2$, 1.2 mM MgCl$_2$, 20 mM Tris HCl, 12 mM glucose, pH 7.4) and 0.025 ml of various drug solutions in 48% Ethanol. The tubes are pre-incubated for 30 min on ice and then for 6 min at 37° C. in a water bath.

The uptake is immediately initiated by adding 0.4 ml of $^{45}$CaCl$_2$ (specific activity=29–39 Ci/g; 0.5 Ci/assay), in 145 mM NaCl for non-depolarized samples and in 145 mM KCl for depolarized samples. The incubation is continued for 15 s.

The uptake is terminated by rapid filtration through GF-C glass fiber filters which are washed three times with 5 ml of a cold solution containing 145 mM KCl, 7 mM EGTA and 20 mM Tris HCl, pH 7.4. The amount of radioactivity on the filter disc is determined by liquid scintillation spectrometry.

TEST PROCEDURE

Test substances are dissolved in 10 ml of 48% ethanol at a concentration of 0.44 mg/ml. Dilutions are made in 48% ethanol to give final concentrations of 0.1, 0.3, 1, 3 and 0 10 µg/ml. Experiments are performed in duplicate. Controls for depolarized and nondepolarized samples are included in the assay and test substances are only tested in depolarized samples. 25–75% inhibition of stimulated uptake must be obtained before calculating the IC$_{50}$ value.

RESULTS

The test value will be given as IC$_{50}$ (the concentration (µg/ml) of test substance which inhibit 50% of stimulated uptake of $^{45}$Ca (uptake in depolarized samples corrected for basal uptake in nondepolarized samples )). The IC$_{50}$ value is estimated from dose response curves.

Test results obtained by testing some compounds of the present invention will appear from the following table 1.

TABLE 1

[Structure: piperidine with 4-phenyl (bearing X substituent), 3,4-trans, CH$_2$OR$^3$ at position 3, N-R$^1$]

| R$^1$ | R$^3$ | X | optic form | IC$_{50}$ µg/ml |
|---|---|---|---|---|
| —(CH$_2$)$_3$CH$_3$ | benzo[1,3]dioxol-5-yl-methylene | 4-F | (−) | 1.9 |
| —(CH$_2$)$_3$CH$_3$ | 4-methoxybenzyl | 4-F | (−) | 2.3 |
| —CH(CH$_3$)$_2$ | 4-methoxybenzyl | 4-F | (−) | 4.3 |
| —(CH$_2$)$_7$CH$_3$ | benzo[1,3]dioxol-5-yl-methylene | 4-F | (−) | 2.2 |
| —(CH$_2$)$_4$CH$_3$ | benzo[1,3]dioxol-5-yl-methylene | 4-F | (−) | 1.5 |

TABLE 1-continued

Structure: 3,4-trans piperidine with X-phenyl at C4, CH₂OR³ at C3, N-R¹

| R¹ | R³ | X | optic form | IC₅₀ μg/ml |
|---|---|---|---|---|
| —CH₂CH₃ | 4-C(CH₃)₃-phenyl | 4-F | rac | 2.5 |
| —CH₂—CH=CH₂ | 3,4-methylenedioxyphenyl | 4-F | (−) | 0.8 |
| —(CH₂)₄CH₃ | 3,4-methylenedioxyphenyl | H | (+) | 2.4 |
| —(CH₂)₄CH₃ | 5,6,7,8-tetrahydronaphthalen-2-yl | 4-F | (−) | 0.4 |
| Nifedipin* | | | | 26 |
| Verapamil* | | | | 16 |
| Diltiazem* | | | | >90 |

*Well known calcium antagonists

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and, in such form may be employed as solids, such as tablets or filled capsules; or liquids, such as solutions, suspensions, emulsions, elixirs, or capsules filled with the same, all for oral use; in the form of suppositories for rectal administration: or in the form of sterile injectable solutions for parenteral (including subcutneous) use. Such pharmaceutical compositions and unit dosage forms thereof may comprise conventional ingredients in conventional proportions, with or without additional active compounds or principles, and such unit dosage forms may contain any suitable effective calcium overload blocking amount of the active ingredient commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixirs or the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 10–100 mg/day, when administered to patients, e.g. humans, as a drug.

A typical tablet which may be prepared by conventional tabletting techniques contains:

| | |
|---|---|
| Active compound | 5.0 mg |
| Lactosum | 67.8 mg Ph.Eur. |
| Avicel TM | 31.4 mg |
| Amberlite TM IRP 88 | 1.0 mg |
| *Magnesii stearas* | 0.25 mg Ph.Eur. |

Due to the high calcium overload blocking activity, the compounds of the invention are extremely useful in the treatment of symptoms related to an accumulation of calcium in brain cells of mammals, when administered in an amount effective for blocking calcium overload in brain cells. The important calcium overload blocking activity of compounds of the invention includes both activity against anoxia, ischemia, migraine and epilepsy. The compounds of the invention may accordingly be administered to a subject, e.g., a living animal body, including a human, in need of a calcium overload blocker, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective calcium overload blocking amount, and in any event an amount which is effective for the treatment of anoxia, ischemia, migraine or epilepsy due to their calcium overload blocking activity. Suitable dosage ranges are 1–200 milligrams daily, 10–100 milligrams daily and especially 30–70 milligrams daily depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

Example 1

(−)-trans-4-(-4-fluorophenyl)-3-(3,4-methylenedioxyphenoxymethyl)-1-pentylpiperidine hydrochloride 10g of (−)-trans-4-(-4-fluorophenyl)-3,4-methylenedioxyphenoxymethyl)-piperidine hydrochloride in 250 ml 99.9% ethanol was mixed with 50 ml 1-bromopentane and 20 g potassium carbonate. The mixture was refluxed for 3 hours and was subsequently cooled to room temperature. 25 ml acetone and 25 ml diethylether was added to the solution. The precipitate was filtered off and the filtrate was evaporated in vacuo. 20 ml 4N NaOH was added to the residue, and the resulting mixture was extracted 3 times with diethyl ether. The combined ether phases were dried over potassium carbonate, filtered, the filtrate was acidified with conc. hydrochloric acid to pH 2, and the filtrate was evaporated in vacuo. The resulting oil was dissolved in acetone and crystals precipitated by addition of ether and after cooling at 4° C. over night. The title compound was filtered off and dried giving 10.1 g of the title compound. M.p. 153.6° C.

The following compounds were prepared in exactly the same manner from (−)-trans-4-(-4-fluorophenyl)-3-(3,4-methylendioxyphenoxymethyl)-piperidine hydrochloride and the corresponding alkyl bromide, alkoxyalkyl bromide, cycloalkyl bromide, aryloxyalkyl bromide, or alkenyl bromide.

(−)-trans-4-(-4-fluorophenyl)-3-(3,4-methylenedioxyphenoxymethyl)-1-ethylpiperidine hydrochloride M.p. 237°–238° C. by refluxing the reaction mixture for 24 hours.

(−)-trans-4-(-4-fluorophenyl)-3-(3,4-methylenedioxyphenoxymethyl)-1-propylpiperidine hydrochloride M.p. 198.3° C. by refluxing the reaction mixture for 7 hours.

(−)-trans-4-(-4-fluorophenyl)-3-(3,4-methylenedioxyphenoxymethyl)-1-butylpiperidine hydrochloride M.p. 190°–191° C. by refluxing the reaction mixture for 7 hours.

(−)-trans-4-(-4-fluorophenyl)-3-(3,4-methylenedioxyphenoxymethyl)-1-octylpiperidine hydrochloride M.p. 167.3° C. by refluxing the reaction mixture for 72 hours.

(−)-trans-4-(-4-fluorophenyl)-3-(3 4-methylenedioxyphenoxymethyl)-1-isopentylpiperidine hydrochloride M.p. 152.620 C. by refluxing the reaction mixture for 6 hours.

(−)-trans-4-(-4-fluorophenyl)-3-(3,4-methylenedioxyphenoxymethyl)-1-(4-phenoxybutyl)-piperidine hydrochloride as an oil by refluxing the reaction mixture for 240 hours.

(−)-trans-4-(-4-fluorophenyl)-3-(3,4-methylenedioxyphenoxymethyl)-1-hexylpiperidine hydrochloride M.p. 107.1° C. by refluxing the reaction mixture for 24 hours.

(−)-trans-4-(-4-fluorophenyl)-3-(3,4-methylenedioxyphenoxymethyl)-1-(3-phenylpropyl)-piperidine hydrochloride as an oil by refluxing the reaction mixture for 3.5 hours.

(−)-trans-4-(-4-fluorophenyl)-3-(3,4-methylenedioxyphenoxymethyl)-1-(2-ethylhexyl)-piperidine hydrochloride as an oil by refluxing the reaction mixture for 240 hours.*

(−)-trans-4-(-4-fluorophenyl)-3-(3,4-methylenedioxyphenoxymethyl)-1-(3,3-dimethylbutyl)-piperidine hydrochloride M.P. 226.7° C. by refluxing the reaction mixture for 336 hours *

(−)-trans-4-(-4-fluorophenyl)-3-(3,4-methylenedioxyphenoxymethyl)-1-cyclohexyl-piperidine hydrochloride M.p. 140.2° C. by refluxing the reaction mixture for 330 hours.*

(−)-trans-4-(-4-fluorophenyl)-3-(3,4-methylenedioxyphenoxymethyl)-1-heptyl-piperidine hydrochloride M.p. 146.8° C. by refluxing the reaction mixture for 6 hours.

(−)-trans-4-(-4-fluorophenyl)-3-(3,4-methylenedioxyphenoxymethyl)-1-cyclopentyl-piperidine hydrochloride M.p. 227.7° C. by refluxing the reaction mixture for 7 hours.

(−)--trans-4-(-4-fluorophenyl)-3-(3,4-methylenedioxyphenoxymethyl)-1-allyl-piperidine hydrochloride M.p. 162.2° C. by refluxing the reaction mixture for 24 hours.

(—)-trans-4-(-4-fluorophenyl)-3-(2,4-methylenedioxyphenoxymethyl)-1-cyclopropylmethylpiperidine hydrochloride M.p. 175.5° C. by refluxing the reaction mixture for 24 hours.

(—)-trans-4-(-4-fluorophenyl)-3-(3,4-methylenedioxyphenoxymethyl)-1-cycloheptyl-piperidine hydrochloride as an glas M.p. 53.7° C. by refluxing the reaction mixture for 190 hours.* and **

(—)-trans-4-(-4-fluorophenyl)-3-(3,4-methylenedioxyphenoxymethyl)-1-(2-ethoxyethyl)-piperidine hydrochloride as an glass M.p. 49.5° C. by refluxing the reaction mixture for 6 hours.

(—)-trans-4-(-4-fluorophenyl)-3-(3,4-methylenedioxyphenoxymethyl)-1-(2-methoxymethyl)-piperidine hydrochloride M.p. 164.7° C. by refluxing the reaction mixture for 48 hours.

(—)-trans-4-(-4-fluorophenyl)-3-(3,4-methylenedioxyphenoxymethyl)-1-(2-trans-butenyl)-piperidine hydrochloride M.p. 195.5° C. by refluxing the reaction mixture for 3 hours.

(—)-trans-4-(-4-fluorophenyl)-3-(3,4-methylenedioxyphenoxymethyl)-1-(3-butenyl)-piperidine hydrochloride M.p. 198.6° C. by refluxing the reaction mixture for 288 hours.

(—)-trans-4-(-4-fluorophenyl)-3-(3,4-methylenedioxyphenoxymethyl)-1-(5-hexenyl)-piperidine hydrochloride M.p. 123° C. by refluxing the reaction mixture for 3 hours.

(—)-trans-4-(-4-fluorophenyl)-3-(3,4-methylenedioxyphenoxymethyl)-1-(4-pentenyl)-piperidine hydrochloride M.p. 177.7° C. by refluxing the reaction mixture for 3 hours.

(—)-trans-4-(-4-fluorophenyl)-3-(3,4-methylenedioxyphenoxymethyl)-1-(3-methyl-butenyl)-piperidine hydrochloride M.p. 239.2° C. by refluxing the reaction mixture for 4.5 hours.

* The crude compound was purified on a silicagel column using 99.9% ethanol as eluent. The eluent solution was acidified and the title compound was isolated as described above, i.e. by evaporation, dissolution in acetone and precipitation by addition of diethyl ether.
** 1-Butanol was used as solvent instead of ethanol.

(—)-cis-4-(-4-fluorophenyl)-3-(3,4-methylenedioxyphenoxymethyl)-1-pentylpiperidine hydrochloride M.p. 195.3° C. and (+)-cis-4-(-4-fluorophenyl)-3-(3,4-methylenedioxyphenoxymethyl)-1-pentylpiperidine hydrochloride M.p. 193.7° C. were prepared exactly as described above from pentyl bromide, and (—)-cis-4-(-4-fluorophenyl)-3-(3,4-methylenedioxyphenoxymethyl)-piperidine hydrochloride and (+)-cis-4-(-4-fluorophenyl)-3-(3,4-methylendioxyphenoxymethyl)-piperidine hydrochloride respectively.

Example 2

(—)-trans-1-butyl-4-(4-fluorophenyl)-3-(4-methoxyphenoxymethyl)-piperidine hydrochloride (—)-trans-1-butyl-4-(4-fluorophenyl)-3-(4-methoxyphenoxymethyl)-piperidine hydrochloride M.p. 163°–165° C. was prepared exactly as described in Example 1 from (—)-trans-4-(4-fluorophenyl)-3-(4-methoxyphenoxymethyl)-piperidine hydrochloride and butyl bromide by refluxing for 120 hours.

The following compounds were prepared in exactly the same manner from (—)-trans-4-(4-fluorophenyl)-3-(4-methoxyphenoxymethyl)-piperidine hydrochloride and the corresponding alkyl bromide or cycloalkyl bromide.

(—)-trans-1-propyl-4-(4-fluorophenyl)-3-(4-methoxyphenoxymethyl)-piperidine hydrochloride M.p. 196°–197° C. by refluxing the reaction mixture for 7 hours.

(—)-trans-1-ethyl-4-(4-fluorophenyl)-3-(4-methoxyphenoxymethyl)-piperidine hydrochloride M.p. 190°–191° C. by refluxing the reaction mixture for 170 hours.

(—)-trans-1-isopropyl-4-(4-fluorophenyl)-3-(4-methoxyphenoxymethyl)-piperidine hydrochloride as an oil by refluxing the reaction mixture for 210 hours.

(—)-trans-1-(2-(4-methoxyphenoxyethyl))-4-(4-fluorophenyl)-3-(4-methoxyphenoxymethyl)-piperidine hydrochloride as an oil by refluxing the reaction mixture for 48 hours.

(—)-trans-1-pentyl-4-(4-fluorophenyl)-3-(4-methoxyphenoxymethyl)-piperidine hydrochloride as a glass M.p. 53.5° C. by refluxing the reaction mixture for 8 hours.

(—)-trans-1-heptyl-4-(4-fluorophenyl)-3-(4-methoxyphenoxymethyl)-piperidine hydrochloride M.p. 138.1° C. by refluxing the reaction mixture for 8 hours.

(—)-trans-1-cyclohexyl-4-(4-fluorophenyl)-3-(4-methoxyphenoxymethyl)-piperidine hydrochloride M.p. 220.3° C. by refluxing the reaction mixture for 330 hours.**

** 1-Butanol was used as solvent instead of ethanol.

Example 3 trans-1-propyl-4-(4-fluorophenyl)-3-(4-t-butylphenoxymethyl)-piperidine hydrochloride trans-1-propyl-4-(4-fluorophenyl)-3-(4-t-butylphenoxymethyl)-piperidine hydrochloride M.p. 221° C. was prepared exactly as described in example 1 from trans-4-(4-fluorophenyl)-3-(4-t-butylphenoxymethyl)-piperidine hydrochloride and propyl bromide by refluxing for 96 hours.

The following compounds were prepared in exactly the same manner from trans-4-(4-fluorophenyl)-3-(4-t-butylphenoxymethyl)-piperidine hydrochloride and the corresponding alkyl bromide.

trans-1-ethyl-4-(4-fluorophenyl)-3-(4-t-butylphenoxymethyl)piperidine hydrochloride M.p. 220.6° C.

trans-1-butyl-4-(4-fluorophenyl)-3-(4-t-butylphenoxymethyl)piperidine hydrochloride M.p. 183.1° C.

Example 4

(—)trans-3-(2-Cyclohexylphenoxymethyl)-4-(4-fluorophenyl)1-methyl-piperidine, HCl.

5.13g 2-cyclohexylphenol was dissolved in dry DMF.1.5g NaH (55% oil dispersion) was washed with ether and subsequently added slowly to the solution. When gas evolution had ceased, 6,4 g of (—) trans 3-chloromethyl-4-(4-fluorophenyl)1-methylpiperidine was slowly added and the mixture refluxed for 5h. Subsequently the mixture was left at room temperature overnight, evaporated to dryness in vacuo. The residue was dissolved in dilute NaOH and extracted several times with ether. The etheral layers were dried with $K_2CO_3$, evaporated to dryness and extracted once more from NaOH with ether. The ether layer was extracted with dilute HCl, the acid solution evaporated to dryness and the residue further purified on a silicagel column using $CHCl_3/CH_3OH$ (9/1) as eluent. The compound was isolated from the eluent by evaporation. m.p. 64.9° C. (hard glass)

The following compounds were prepared in the same manner from (−) trans-3-chloromethyl-4-(4-fluorophenyl)-1-methylpiperidine and the appropriate phenol.

-trans 4-(4-Fluorophenyl)-1-methyl-3-(5,6,7,8,-tetrahydro-2-naphthoxymethyl)-piperidine, HCl. m.p. 198.5° C.

-trans 3-(4-Benzyloxyphenoxymethyl)-4-(4-fluorophenyl)-1-methylpiperidine HCl. m.p. 112.5° C.

-trans 3-(4-Benzyloxy-3-methoxyphenoxymethyl)-4-(4-fluorophenyl)-1-methylpiperidine, HCl. m.p. 59.6° C. (hard glass)

-trans 4-(4-Fluorophenyl)-1-methyl-3-(2-naphthoxymethyl)piperidine, HCl. m.p. 214.4° C.

Example 5

A): -trans 3-(2-Cyclohexylphenoxymethyl)-4-(4-fluorophenyl)piperidine, HCl was prepared by means of alpha-chloroethylchloroformate using the method described in J.Org.Chem. 1984:49:2081 (R.A. Olofson, J.T. Martz, J.P. Senet, M. Piteau and T. Malfroot), m.p. 216.7° C.

The following compounds were prepared in exactly the same manner by dealkylation of the corresponding N-methyl-compound.

(+−) trans 3-(4-Benzyloxyphenoxymethyl)-4-phenylpiperidine, HCl. m.p. 132.4° C.

(−) trans 4-(4-Fluorophenyl)-3-(5,6,7,8,-tetrahydro-2-naphthoxymethyl)-piperidine, HCl. m.p. 55.1° C. (hard glass)

(−) trans 3-(4-Benzyloxyphenoxymethyl)-4-(4-fluorophenyl)piperidine m.p. 132.7° C.

(−) trans 3-(2-Benzothiazolylthiomethyl)-4-(4-fluorophenyl)piperidine, HCl. m.p. 72.2° C. (hard glass)

(−) trans 4-(4-Fluorophenyl)-3-(2-naphthoxymethyl)-piperidine, HCl. m.p. 238.6° C.

B): The following compounds were prepared from the corresponding piperidine and alkyl bromide in exactly the same manner as described in Example 1.

(−) trans 3-(2-Cyclohexylphenoxymethyl)-4-(4-fluorophenyl)1-pentylpiperidine, HCl. m.p. 210.3° C. Reaction time 18h.

(+) trans 3-(3,4-Methylenedioxyphenoxymethyl)-1-pentyl-4-phenylpiperidine, HCl. m.p. 175.0° C. Reaction time 2.5h.

(+−) trans 3-(4-Benzyloxyphenoxymethyl)-1-pentyl-4-phenylpiperidine, HCl. m.p. 139.5° C. Reaction time 17h.

(+−) trans 1-Allyl-3-(4-benzyloxyphenoxymethyl)-4-phenylpiperidine, HCl. m.p. 212.1° C. Reaction time 3.5h. Equimolar amounts of piperidine-compound and allyl bromide was used.

(−) trans 3-(4-Methoxyphenoxymethyl)-1-pentyl-4-phenylpiperidine, HCl. m.p. 138.7° C. Reaction time 18h.

(−), trans 1-Allyl-3-(4-methoxyphenoxymethyl)-4-phenylpiperidine, HCl. m.p. 197.5° C. Reaction time 1.5h. Equimolar amounts of allyl bromide and piperidine-compound was used.

(+) trans 3-(4-Methoxyphenoxymethyl)-1-pentyl-4-phenylpiperidine, HCl. m.p. 138.7° C. Reaction time 18.5h.

(+) trans 1-Allyl-3-(4-methoxyphenoxymethyl)-4-phenylpiperidine, HCl. m.p. 195.9° C. Reaction time 20.5h. Equimolar amounts of allyl bromide and piperidine-compound was used.

(−) trans 4-(4-Fluorophenyl)-1-pentyl-3-(5,6,7,8-tetrahydro-2-naphthoxymethyl)-piperidine, HCl. m.p. 55.3° C. (hard glass). Reaction time 2h. The crude product was purified on a silicagel column, $CHCl_3/CH_3OH$ (9/1) as eluent.

(−) trans 3-(2-Benzothiazolylthiomethyl)-4-(4-fluorophenyl)-1-pentylpiperidine, HCl. m.p. 199.9° C. Reaction time 7h.

(−) trans 4-(-Fluorophenyl)-3-(2-naphthoxymethyl)-1-pentylpiperidine, HCl. m.p. 54.6° C. (hard glass). Reaction time 4.5h. The crude product was purified on a silicagel column with $CHCl_3/CH_3OH$ (9/1) as eluent.

(−) trans 1-Butyl-4-(4-fluorophenyl)-3-(5,6,7,8-tetrahydro2-naphthoxymethyl)-piperidine, HCl. M.p. 154.3° C. Reaction time 2.5 h.

(−) trans 4-(4-Fluorophenyl)-1-propyl-3-(5,6,7,8-tetrahydro2-naphthoxymethyl)-piperidine, HCl. M.p. 186.6° C. Reaction time 3.5 h.

(−) trans 4-(4-Fluorophenyl)-1-hexyl-3-(5,6,7,8-tetrahydro2-naphthoxymethyl)-piperidine, HCl. M.p. 146.7° C. Reaction time 4 h. The crude product was purified on a silicagel column with $CHCl_3/CH_3OH$ (9/1) as eluent.

(−) trans 1-Ethyl-4-(4-Fluorophenyl)-3-(5,6,7,8-tetrahydro2-naphthoxymethyl)-piperidine, HCl. M.p. 217.0° C. Reaction time 24 h. The crude product was purified on a silicagel column with $CHCl_3/CH_3OH$ (9/1) as eluent.

Example 6

(−) trans 3-(2-Benzothiazolylthiomethyl)-4-(4-fluorophenyl)-1-methylpiperidine,HCl was prepared by refluxing a mixture of 5g benzothiazol-2-thiol, 7.1g (−) trans-(3-chloromethyl) 4-(4-fluoromethyl)-1-methylpiperidine and 5g potassium carbonate in ethanol for 24h. Acetone/ether was added, the mixture filtered and the filtrate evaporated to drynes. The residue was extracted from NaOH/ether, the ether layer dried with $K_2CO_3$, acidified with conc. HCl to pH2, and evaporated to dryness. The resulting oil was crystallized from acetone/ether. m.p. 204.2° C.

In conclusion, from the foregoing it is apparent that the present invention provides novel effective calcium overload blocking piperidine compounds and salts thereof, having advantageous and unpredictable properties, as well as novel pharmaceutical compositions thereof and a method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art and the invention is therefore to be limited only by the full scope of the appended claims.

We claim:

1. A piperidine compound selected from those having the formula I

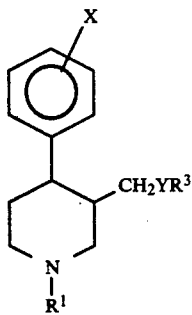

wherein R³ is 3,4-methylenedioxyphenyl, naphthyl or phenyl which may be substituted with one or more C₁₋₆-alkyl, C₁₋₆-alkoxy, C₃₋₈-cycloalkyl, C₃₋₅-alkylene, or benzyloxy groups, R¹ is straight or branched C₅₋₈-alkyl, C₄₋₈-alkenyl, C₄₋₇-cycloalkyl, C₄₋₈-cycloalkylalkyl, phenyllower-alkyl, phenyloxylower-alkyl, and lower-alkoxy-lower-alkyl, X is hydrogen or 4-fluoro and wherein Y is O or S, and a salt thereof with a pharmaceutically-acceptable acid.

2. A compound of claim 1 which is (−)-trans-4-(-4-fluorocyclopentyl)-3-(3,4-methylenedioxyphenoxymethyl)-1-pentylpiperidine hydrochloride.

3. A compound of claim 1 which is (+)-trans-4-phenyl-3-(3,4-methylenedioxyphenoxymethyl)-1-pentylpiperidine hydrochloride.

4. A compound of claim 1 which is (−)-trans-4-(-4-fluorophenyl)-3-(4-methoxyphenoxymethyl)-1-pentylpiperidine hydrochloride.

5. A compound of claim 1 which is (−)-trans-4(-4-fluorophenyl)-3-(5,6,7,8-tetrahydro-2-naphthoxymethyl)-1-pentylpiperidine hydrochloride.

6. A pharmaceutical composition suitable for use in preventing calcium overload in brain cells of mammals, including humans, comprising an amount of a compound of claim 1, which is effective for inhibiting calcium uptake into brain cells, together with a pharmaceutically-acceptable carrier or diluent.

7. A pharmaceutical composition according to claim 6 in the form of an oral dosage unit containing 1–100 mg of the active compound.

8. A compound of claim 1 which is (−)-trans-4-(4-fluorophenyl)-3(3,4-methylenedioxyphenoxymethyl)-1-pentylpiperidine or a pharmaceutically-acceptable salt thereof.

9. A compound of claim 1 which is (−)-trans-4-(4-fluorophenyl)-3-(3,4-methylenedioxyphenoxymethyl)-1-pentylpiperidinee hydrochloride.

* * * * *

UNITED STATES PATENT AND TRADEMARK OFFICE
CERTIFICATE OF CORRECTION

PATENT NO. : 5,019,582

DATED : May 28, 1991

INVENTOR(S) : Jorgen Drejer, Palle Jakobsen

It is certified that error appears in the above-identified patent and that said Letters Patent is hereby corrected as shown below:

```
Column 1, approximately line 24; "i n" should read -- in --.
Column 1, line 51; "3 4" should read -- 3,4 --.
Column 1, line 55; "-alkoxy-", first occurrence, should read
    -- -alkyl, --.
Column 1, line 56; "-alkyl C_{4-8}" should read -- -alkyl, C_{4-8} --
Column 1, line 59; "alkyl C" should read -- alkyl, C --.
Column 2, approximately line 22; delete "the", second occurrence --.
Column 2, line 43; delete "the", second occurrence.
Column 2, line 52; "socalled" should read -- so-called --.
Column 2, line 55; "socalled" should read -- so-called --.
Column 2, line 62; "M P. Mol." should read -- M.P., Mol. --.
Column 4, line 8; "and 0 10" should read -- and 10 --.
Column 7, line 2; "elixirs" should read -- elixir, --.
Column 8, approximately line 31; "-(3   4-" should read
    -- -(3,4- --.
Column 8, line 33; "152.620" should read -- 152.6° --.
Column 9, line 4; "(2,4" should read -- (3,4 --.
Column 9, line 10; "as an glas" should read -- as a glass --.
Column 9, line 14; "as an glass" should read -- as a glass --.
Column 9, approximately line 30; "123° C." should read
    -- 123.1° C. --
Column 10, line 35; "221° C." should read -- 221.1° C. --.
Column 10, line 57; "6,4" should read -- 6.4 --.
Column 10, line 58; "fluorophenyl)1" should read
    -- fluorophenyl)-1 --.
Column 11, line 10; "methylpiperidine HCl." should read
    -- methylpiperidine, HCl. -- .
Column 11, approximately line 43; "phenyl)1" should read
    -- phenyl)-1 --.
Column 11, line 58; "(-), trans"  should read -- (-) trans --.
```

UNITED STATES PATENT AND TRADEMARK OFFICE
CERTIFICATE OF CORRECTION

PATENT NO. : 5,019,582

DATED : May 28, 1991

INVENTOR(S) : Jorgen Drejer, Palle Jakobsen

It is certified that error appears in the above-identified patent and that said Letters Patent is hereby corrected as shown below:

```
Column 12, line 10; "(-Fluorophenyl)" should read
    -- (4-Fluorophenyl) --.
Column 12, line 17; "dro2-" should read -- dro-2- --.
Column 12, approximate line 21; "rahydro2-" should read
    -- rahydro-2- --.
Column 12, line 24; "rahydro2-" should read -- rahydro-2- --.
Column 12, approximately line 30; "rahydro2-" should read
    -- rahydro-2- --
Column 12, line 41; "(3-chloromethyl)  4-" should read
    -- (3-chloromethyl)-4- --.
Column 14, line 2; "fluorocyclopentyl)-3" should read
    -- fluorophenyl)-3 --. (Claim 2)
Column 14, line 3; "pentylpiperidine" should read
    -- cyclopentylpiperidine --.
Column 14, line 28; "pentylpiperidinee" should read
    -- pentylpiperidine --.
```

Signed and Sealed this

Third Day of November, 1992

*Attest:*

DOUGLAS B. COMER

*Attesting Officer*   *Acting Commissioner of Patents and Trademarks*